(12) United States Patent
Cai

(10) Patent No.: US 11,598,942 B2
(45) Date of Patent: Mar. 7, 2023

(54) MULTI-CHANNEL LINE SCANNER FOR FAST LARGE FIELD AND CONFOCAL IMAGING

(71) Applicant: California Institute of Technology, Pasadena, CA (US)

(72) Inventor: Long Cai, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 370 days.

(21) Appl. No.: 16/677,482

(22) Filed: Nov. 7, 2019

(65) Prior Publication Data

US 2020/0142170 A1    May 7, 2020

Related U.S. Application Data

(63) Continuation of application No. PCT/US2019/059550, filed on Nov. 1, 2019.
(Continued)

(51) Int. Cl.
*G02B 21/00* (2006.01)
*G16B 35/00* (2019.01)
*G01N 21/64* (2006.01)

(52) U.S. Cl.
CPC ..... *G02B 21/0076* (2013.01); *G01N 21/6458* (2013.01); *G02B 21/0036* (2013.01); *G16B 35/00* (2019.02)

(58) Field of Classification Search
CPC ............ G02B 21/0076; G02B 21/0036; G02B 21/00; G02B 21/0004; G02B 21/002;
(Continued)

(56) References Cited

U.S. PATENT DOCUMENTS

| 2010/0238442 | A1  | 9/2010  | Heng et al. |
| 2012/0257196 | A1* | 10/2012 | Raicu ........................ G01J 3/06 356/300 |
| 2013/0250088 | A1* | 9/2013  | Osipchuk ........... G02B 21/0064 348/79 |

FOREIGN PATENT DOCUMENTS

| CN | 108121060 A | 6/2018 |
| DE | 102012203736 A1 | 9/2013 |

(Continued)

OTHER PUBLICATIONS

International Search Report and Written Opinion dated Jul. 3, 2020 for International Application No. PCT/US2019/059550, 21 pages.
(Continued)

*Primary Examiner* — Arnel C Lavarias
(74) *Attorney, Agent, or Firm* — Squire Patton Boggs (US) LLP

(57) ABSTRACT

A multi-channel line microscope for single molecule Fluorescence In Situ Hybridization (FISH) imaging of a sample. A microscope stage moves a sample across two or more reflected excitation lines positioned relative to each other so that each excitation line excites a spatially distinct horizontal line in the image plane of the sample. A sample is imaged by moving the microscope stage across two or more reflected excitation lines positioned relative to each other so that each excitation line excites a spatially distinct horizontal line in the image plane of the sample. The apparatus and methods of use are suitable for a broad range of applications.

12 Claims, 6 Drawing Sheets

Related U.S. Application Data

Figure 1:
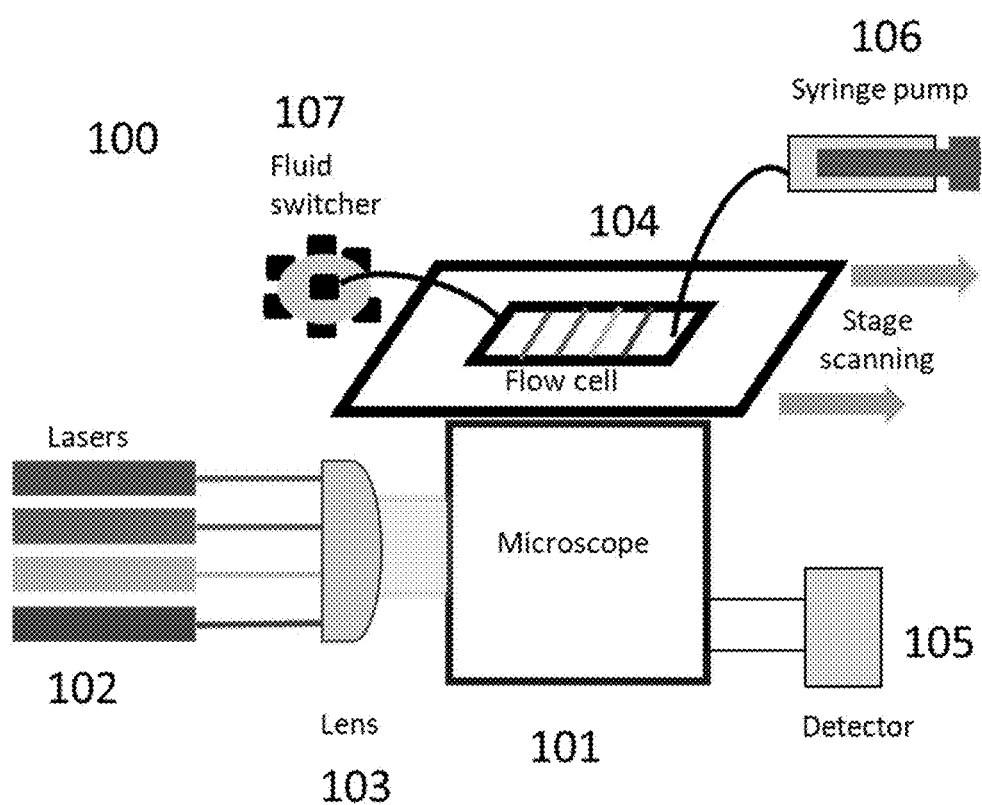

(60) Provisional application No. 62/754,158, filed on Nov. 1, 2018.

(58) Field of Classification Search
CPC ............ G02B 21/0032; G02B 21/0052; G02B 21/0064; G02B 21/06; G02B 21/36; G02B 21/361; G01N 21/6458; G01N 21/6428; G01N 21/6456; G01N 2021/6463; G01N 2021/6478; G01N 21/6486; G16B 35/00
USPC .......................... 359/385, 362, 363, 368, 369
See application file for complete search history.

(56) References Cited

FOREIGN PATENT DOCUMENTS

| WO | WO 2006/128442 A1 | 12/2006 | |
|---|---|---|---|
| WO | WO-2013184758 A2 * | 12/2013 | ......... G01N 21/6456 |
| WO | WO 2017/174795 A2 | 10/2017 | |

OTHER PUBLICATIONS

Invitation to Pay Additional Fees, and partial Search Report, mailed Apr. 3, 2020 for International Application No. PCT/US2019/059550, 16 pages.

Lubeck, et al., "Single-cell in situ RNA profiling by sequential hybridization", Nature Methods Apr. 1, 2014; vol. 11, No. 4, pp. 360-361.

Lubeck, et al., "Single-cell systems biology by super-resolution imaging and combinatorial labeling", Nature Methods Jul. 31, 2012; vol. 9, No. 7, pp. 743-746.

Mohan, et al., "Three Dimensional Fluorescence Imaging using multiple light-sheet microscopy", PLOS ONE Jun. 9, 2014, vol. 9, No. 6, pp. 6-7.

Yen, et al., "3D Modeling of chromosomes territories in normal and aneuploidy nuclei", Progress in Biomedical Optics and Imaging SPIE, International Society for Optical Engineering, Mar. 12, 2018, vol. 10578, p. 4.

* cited by examiner

MULTI-CHANNEL LINE SCANNER FOR FAST LARGE FIELD AND CONFOCAL IMAGING

CROSS-REFERENCE TO RELATED APPLICATIONS

This application is a continuation of International Patent Application No. PCT/US2019/059550, entitled "A Multi-Channel Line Scanner for Fast Large Field and Confocal Imaging," filed Nov. 1, 2019, which claims priority to U.S. Provisional Application Ser. No. 62/754,158, filed Nov. 1, 2018, the entirety of each of which is incorporated herein by reference.

FIELD

The present disclosure relates to a microscope system that allows for analysis of a biological sample. The present disclosure also relates to a method of using the microscope system to analyze a biological sample.

BACKGROUND

Using microscopy, cellular imaging has provided valuable information regarding the abundance of cellular proteins, DNA, and RNA. Cellular imaging has also provided valuable information regarding protein-protein interactions.

There are various types of microscopy including phase contrast, electron, and fluorescence. Fluorescence microscopy is a popular method in biological research and utilizes fluorescence and phosphorescence to study various cellular properties. Fluorescence microscopy makes use of a vast array of fluorochromes that makes it possible to identify cellular components with high specificity amid non-fluorescing material. These fluorochromes are capable of incorporation into molecules that bind selectively to nucleic acids, proteins, or other cellular components. Alternatively, fluorochromes may also be selectively incorporated within nucleic acids, proteins, or other cellular components directly.

SUMMARY

The present disclosure provides a method for imaging a sample by moving a microscope stage across two or more excitation lines positioned so that each excitation line excites a spatially distinct horizontal line in the image plane of the sample. The present disclosure also provides an apparatus for imaging a sample by moving a microscope stage across two or more reflected excitation lines positioned relative to each other so that each excitation line excites a spatially distinct horizontal line in the image plane of the sample. This disclosure sets forth processes, in addition to making and using the same, and other solutions to problems in the relevant field.

In some embodiments, there is provided a method of imaging a sample, comprising: placing the sample on a microscope stage, wherein the sample comprises one or more targets and one or more probes, wherein the probes are capable of emitting visually detectable signals, and wherein each individual probe is hybridized to a unique target in the sample; moving the microscope stage in a single direction linearly or circularly; exciting one or more probes with excitation lines, wherein two or more excitation lines are positioned relative to each other such that each excitation line excites a spatially distinct horizontal line in the image plane of the sample; and detecting one or more signals emitted by the one or more probes.

In some embodiments, there is provided a line scanning system, comprising: a microscope comprising a stage; a sample on the stage, wherein the sample comprises one or more targets and one or more probes, wherein the probes are capable of emitting detectably visual signals, and wherein each individual probe is hybridized to a unique target in the sample; a control unit, configured to control the velocity of the stage across the field of view of the microscope; a line generator, configured to excite a plurality of spatially distinct horizontal lines in the image plane of the sample, such that the horizontal lines are non-overlapping; and a signal detector, capable of detecting signals from the targets.

In some embodiments, there is provided a method for multi-channel imaging a sample, comprising the steps of: providing a sample; illuminating the sample with a plurality of lines of different wavelengths; detecting emission in a plurality of channels with one or more detectors configured to detect emissions along the above lines.

In some embodiments, there is provided an apparatus comprising: a sample support; an illumination component capable of illuminating a plurality of excitation lines of different wavelengths; and detection component capable of detecting the excitation lines.

BRIEF DESCRIPTIONS OF THE DRAWINGS

FIG. 1. A schematic of a multi-channel line scanning microscope as disclosed within the specification.

Figure 2:
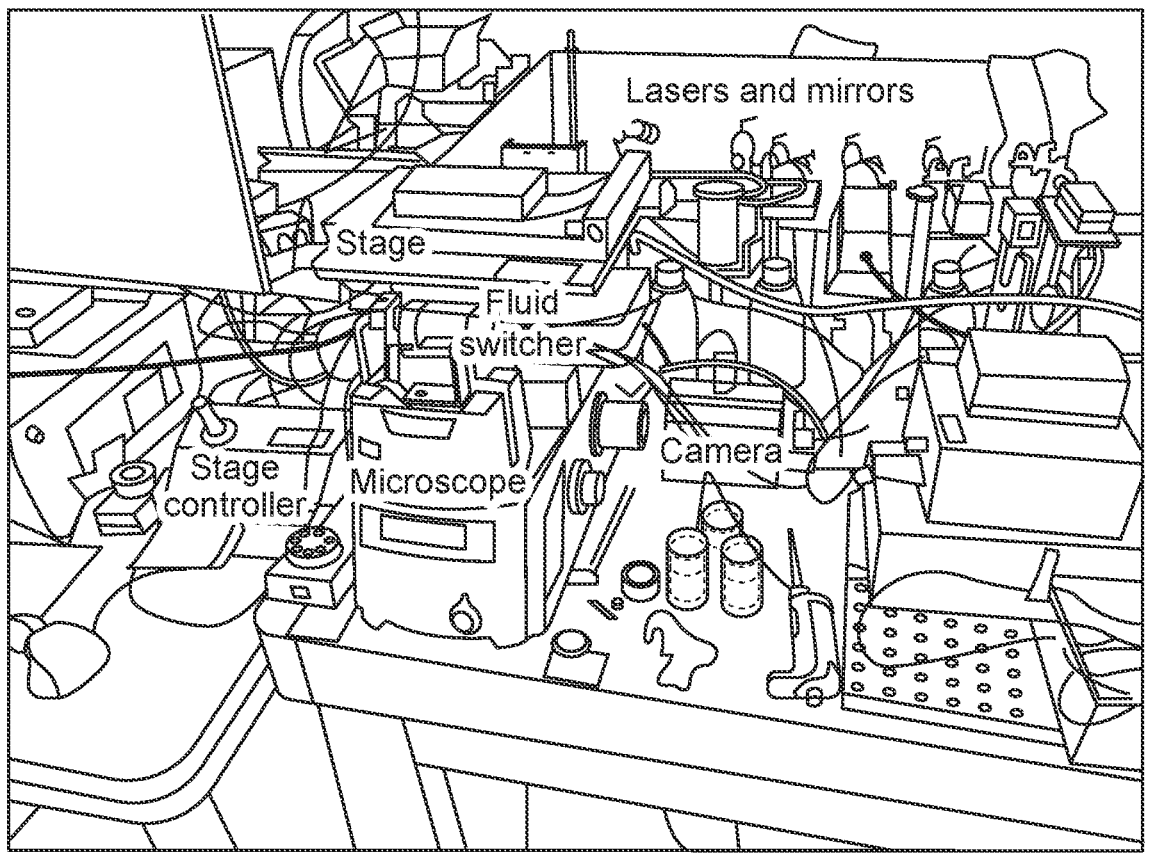
Figure 2:
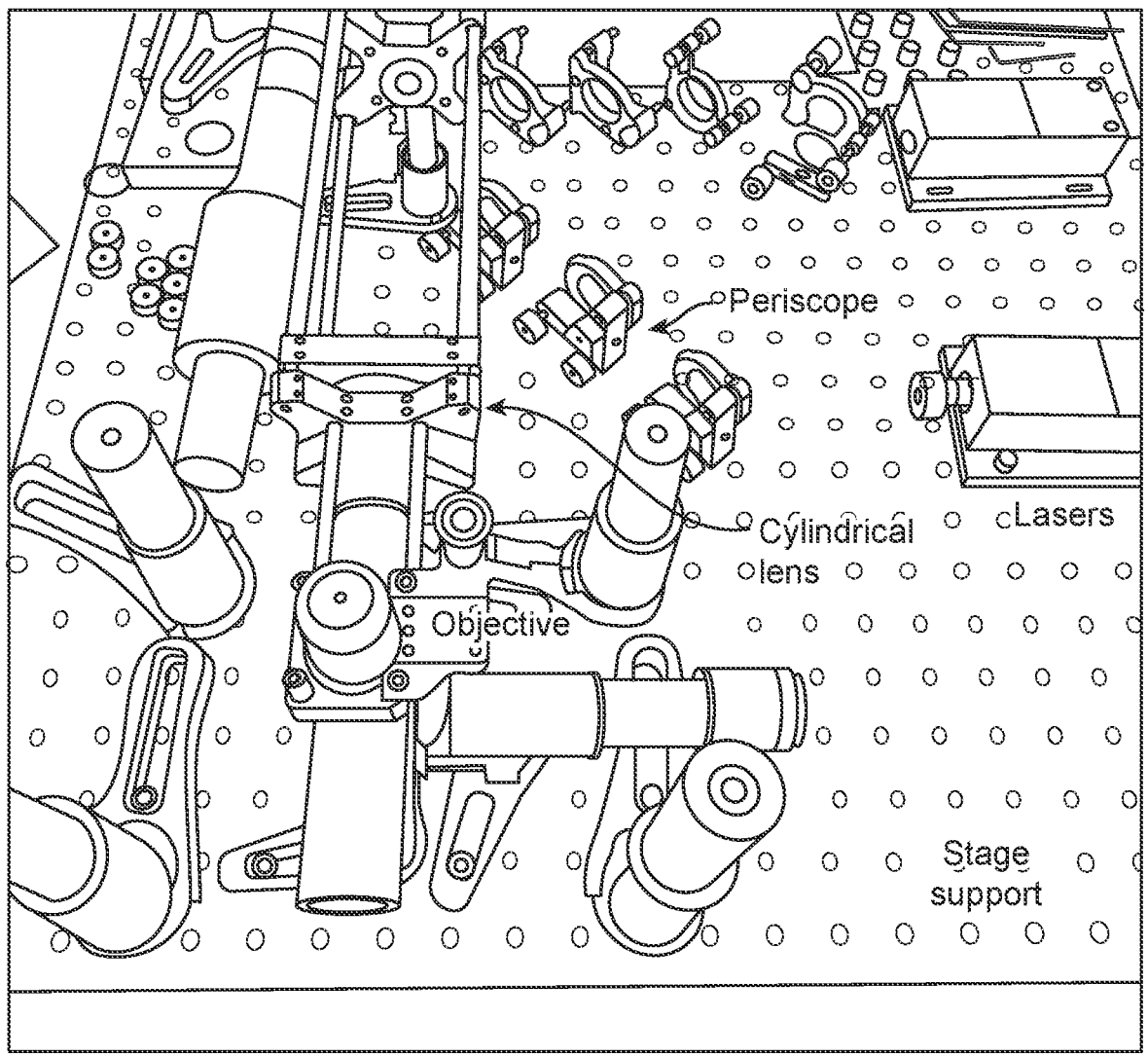

FIG. 2. A schematic display of exemplary assemblies A and B for the multi-channel line scanning microscope.

Figure 3:
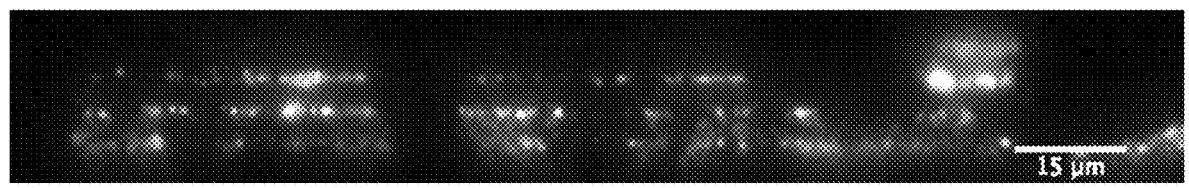

FIG. 3. A 4-channel (405, 488, 556 and 640 nm) line scan image of a brain section using four different lasers, set to different wavelengths, that are focused onto adjacent lines (top to bottom).

Figure 4:
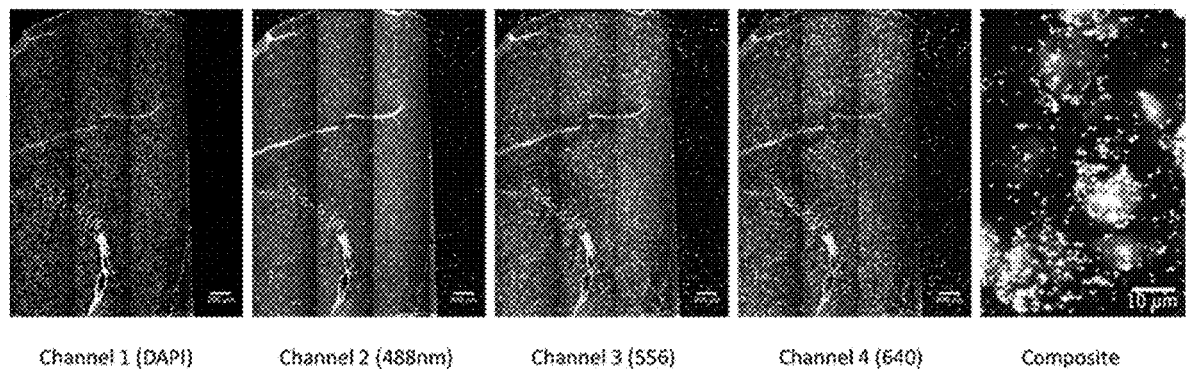

FIG. 4. A multi-channel reconstruction of images of a brain slice using fluorescently labelled mRNA probes.

Figure 5:
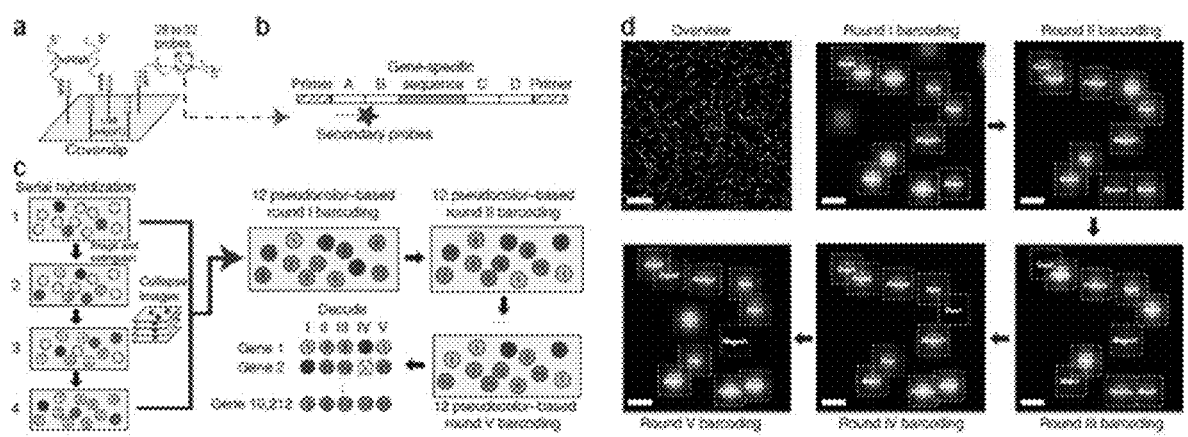

FIG. 5. An exemplary use of the multi-channel line scanning microscope for transcriptional profiling in vitro with RNA SPOTs.

DETAILED DESCRIPTION

The following description is presented to enable one of ordinary skill to make and use the disclosed subject matter and to incorporate it in the context of applications. Various modifications, as well as a variety of uses in different applications, will be readily apparent to those skilled in the art, and the general principles defined herein may be applied to a wide range of embodiments. Thus, the present disclosure is not intended to be limited to the embodiments presented, but is to be accorded the widest scope consistent with the principles and novel features disclosed herein.

Definitions

As used herein, the term "sample" or "biological sample," refers to a biological sample obtained or derived from a source of interest, as described herein. In some examples a sample comprises a biological sample from a source of interest. In certain embodiments, a source of interest comprises an organism, such as an animal or human. In some embodiments, a biological sample comprises biological tissue or fluid. In some embodiments, a biological sample is or comprises bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

As used herein, the terms "approximately" or "about" in reference to a number includes numbers that fall within a range of 5%, 10%, 15%, or 20% in either direction (greater than or less than) of the number unless otherwise stated or otherwise evident from the context (except where such number would be less than 0% or exceed 100% of a possible value).

As used herein, the term "excitation source" refers to any light source including those selected from lasers, LED, lamps, xenon arcs, strobe lighting, pulse lasers, and mercury-vapor lamps capable of emitting light.

As used herein, the term "emission" refers to the emission spectrum that a fluorophore emits in response to the absorption of light at a specific frequency.

As used herein the term "detection channel" or "channel" refers to a predefined wavelength of light that is collected from the range of wavelengths of radiation emitted by a fluorophore as a result of absorbing a specific wavelength of light.

As used herein, the term "oligonucleotide" refers to a polymer or oligomer of nucleotide monomers, containing any combination of nucleobases, modified nucleobases, sugars, modified sugars, phosphate bridges, or modified bridges. An oligonucleotide is between 2 to about 200 nucleotides in length.

As used herein, the term "multi-channel line scanner" refers to the multi-channel line scanning microscope as disclosed herein.

As used herein, the term "constant velocity" refers to a mass moving at a velocity that would be recognized as constant by the person of skill in the art. In certain embodiments, a constant velocity varies by no more than ±20%, ±15%, ±10%, or ±5% of a mean velocity.

As used herein, the term "stage" refers to the microscope stage wherein an experimenter places a sample for analysis.

As used herein, the term "target" refers to a nucleic acid, DNA, RNA, peptide, or protein, under investigation.

As used herein, the term "probe" refers to an oligonucleotide linked to a fluorophore, the oligonucleotide capable of selectively binding to a target molecule.

As used herein, the term "oligonucleotide probe" refers to an oligonucleotide attached to a fluorophore.

As referred herein, the term "visual signal" or "signal" refers to the emission of a fluorophore upon excitation by a specific wavelength of light.

As used herein, the term "detectably labelled oligonucleotide" is synonymous with oligonucleotide probe.

As referred herein, the term "hybridizing" or "hybridization" refers to the process where a nucleic acid probe binds selectively to a single-stranded nucleic acid (DNA or RNA) whose base sequence allows complementarity between the probe and target.

As referred herein, the term "linear movement" refers to the movement of an object from one place to another in a straight or mostly straight line.

As referred herein, the term "circular movement" refers to the movement of an object from one place to another in a circular or mostly circular path.

As referred herein, the term "lens" refers to transparent substance with curved sides for concentrating or dispersing light rays.

As used herein, the term "detector" refers to a device capable of detecting the presence or the absence of a visual signal.

As used herein, the term "computer processor" or "processor" refers to a device capable of receiving input and providing appropriate output. The processor handles all basic system instructions from the user.

As used herein, the term "data storage component" refers to a device interacting with the computer processor that is capable of storing data obtained from experimentation. The data storage component is capable of storing instructions for use in controlling a system to which the data is stored.

As used herein, the term "antibody" refers to any macromolecule that would be recognized as an antibody by those of skill in the art. In some embodiments, an antibody includes any form of an antibody other than the full length form that would be recognized by an antibody fragment by those of skill in the art.

As used herein, the term "unit of exposure time" refers to a particular time interval for which a sample is exposed to light of a particular frequency or frequencies that would be recognized as a unit of exposure time by a person of skill in the art.

As used herein, the term "pixel" refers to the smallest single component of a digital image that would be recognized as a pixel by the person of skill in the art.

As used herein, the term "ultra-violet" refers to the wavelength of light between 10 nm and 400 nm.

As used herein, the term "x-ray" refers to the wavelength of light between 0.01 nm and 10 nm.

As used herein, the term "visible range" refers to the wavelength of light between 380 nm and 740 nm.

As used herein, the term "infrared" refers to the wavelength of light between 740 nm and 1 mm.

As used herein, the term "far infrared" refers to the wavelength of light between 15 μm to 1 mm.

As used herein, the term "radio waves" refers to the wavelength of light between 1 mm to 100 km.

As used herein, the term "microwaves" refers to the wavelength of light between 1 mm to 1 m.

As used herein, the term "lines" refers to any geometric shape or geometric configuration. In some embodiments, lines comprise geometric lines. In some embodiments, lines comprise spots or geometric circles. In some embodiments, lines comprise a geometric parallel configuration. In some embodiments, lines comprise a geometric perpendicular configuration. In some embodiments, lines intersect at an angle or could intersect at an angle if extended. In certain embodiments, lines are straight and parallel.

As used herein, the term "illumination geometry" refers to the arrangement the components of a microscope allowing for the transmission of light of a particular wavelength on a sample and its detection.

As used herein, the term "natural illumination" refers to natural sources of light. In some embodiments, natural sources of light include but are not limited to sunlight; starlight, fire, electricity storms, and bioluminescence.

In this disclosure, a line scanning system and a method of imaging a sample are presented for imaging a sample by moving a microscope stage across two or more excitation lines positioned so that each excitation line excites a spatially distinct horizontal line in the image plane of the sample.

The disclosure herein sets forth embodiments for a line scanning system. The line scanning system herein comprises a microscope, a sample stage, a line generator which is configured to excite a plurality of spatially distinct horizontal lines in the image plane of the sample, such that the horizontal lines are non-overlapping, and a detector.

This disclosure herein sets forth embodiments for an apparatus comprising: a sample support; an illumination component; and detection component.

The disclosure herein sets for embodiments for a method of imaging a sample. The methods herein comprise placing the sample comprising one or more targets and one or more probes on a microscope stage, moving the microscope stage in a single direction, exciting one or more probes with excitation lines, and detecting one or more signals emitted by the one or more probes.

This disclosure herein sets forth embodiments for a method of imaging a sample. The methods herein comprise providing a sample; illuminating the sample with a plurality of lines of different wavelengths; detecting emission in a plurality of channels with one or more detectors configured to detect emissions along the above lines.

Conventional fluorescence microscopy typically utilizers a light source at a specified wavelength, to excite a sample containing a fluorophore. The light emitted from the excited fluorophore is usually collected through a dichroic mirror and an emission filter and constitutes a single channel image. To acquire different channel images, different excitation source wavelengths, dichroic mirrors, and filters are typically needed.

Two common modes of imaging are wide-field and line (or point) scanning. Line scanning has various advantages in terms of data collection over wide-field. In wide-field imaging, each field of view (FOV) is captured on a camera. In order to capture a different FOV, the sample is moved to capture another FOV. Imaging and movement of the sample occurs in discrete stages. In contrast, in line scanning, only a single line of the sample is imaged on a detector, and the sample is moved continuously to acquire the next line. A line scanning system can be significantly faster in imaging speed compared to a FOV imaging system.

The continuous motion of the stage in line scanning is an advantage over the discrete jumps of wide-field imaging. In a wide-field FOV imaging system, the stage carrying the sample makes discrete jumps, accelerating from one position and then deaccelerating to stop at the next position. This is problematic as the mass and inertia of the stage, which can be a few kilograms or more, limits how fast the stage can move between two adjacent FOV. In contrast, in line scanning, the inertia of the stage helps maintain constant stage velocity, and data can be collected continuously. However, in both cases, FOVs or lines can then be tiled and stitched together to generate a much larger image of the sample.

Line scanning also offers an additional advantage over wide-field regarding the correct placement of dichroics and filters. In the wide-field imaging mode, a dichroics filter wheel is turned to put the correct combination of dichroics and filters in position. In contrast, in the line scanning mode, the emissions from different channels are split into different channels by dichroics splitters, with all the excitation source lines focused at the same line on the sample, thus eliminating the need to put in the correct combination of dichroics and filters into position.

Multi-Channel Line Scanning Microscope

In some embodiments, provided herein is an apparatus to acquire multi-color fluorescent images with confocal capabilities using a multi-channel line scanning microscope. FIG. 1 illustrates a diagram of an exemplary line scanning system. The microscope system 100, includes the following components: a microscope 101, one or more excitation sources 102, a lens 103, a stage that moves in a linear direction 104; and a detector 105. Additionally, in certain embodiments, the microscope system includes a syringe pump 106, and a fluid switcher 107. In certain embodiments, the system comprises other components that would ordinarily be found in fluorescent microscopes.

In some embodiments, the multi-channel line scanner comprises a line generator that produces excitation lines. In certain embodiments, the line generator is configured to excite a plurality of spatially distinct horizontal lines in the image plane of the sample, such that the horizontal lines are non-overlapping.

In some embodiments, the line generator comprises at least two excitation sources. In certain embodiments, each excitation source is capable of producing light of a specific wavelength. In certain embodiments, each excitation source is a laser.

In some embodiments, the line generator comprises a plurality of excitation sources. In certain embodiments, at least two excitations sources produce light at different wavelengths. In certain embodiments, at least three excitations sources produce light at different wavelengths. In certain embodiments, at least four excitations sources produce light at different wavelengths. In certain embodiments, at least five excitations sources produce light at different wavelengths. In certain embodiments, at least six excitations sources produce light at different wavelengths.

In some embodiments, each excitation source produces light of a wavelength between 350 to 750 nm. In some embodiments, each excitation source emits light at a different wavelength. In certain embodiments, an excitation source produces light at a wavelength of 405 nm. In certain embodiments, an excitation source produces light at a wavelength of 488 nm. In certain embodiments, an excitation source produces light at a wavelength of 556 nm. In certain embodiments, an excitation source produces light at a wavelength of 640 nm. In certain embodiments, the excitation source produces emission lines. In certain embodiments, the wavelength of light includes but is not limited to x-ray, ultra violet, infrared, far infrared, radio waves, and microwaves.

In some embodiments, multiple excitation sources are positioned so that the emitted wavelengths of light are parallel to each other.

In some embodiments, the line generator comprises a lens. In some embodiments, the lens is capable of focusing light from each of the plurality of excitation sources into excitation lines. In certain embodiments, the lens focuses light from two or more excitation sources and directs the excitation lines onto a sample. In certain embodiments, the excitation lines are positioned relative to each other such that each excitation line excites a spatially distinct horizontal line in the image plane of the sample.

In certain embodiments, the lens is a cylindrical lens. In certain embodiments, a single cylindrical lens focuses the light from a plurality of excitation sources into excitation lines. In certain embodiments, the line generator comprises more than one lens.

In some embodiments, the different excitation lines are positioned such that each excitation line is apart from each other. In certain embodiments, the excitation lines are positioned about 100 µm to about 1 mm apart from each other. In certain embodiments, the excitation lines are positioned about 0.5 µm to about 100 µm apart from each other. In certain embodiments, the excitation lines are positioned about 0.5 µm apart from each other. In certain embodiments, the excitation lines are positioned about 1 µm apart from each other. In certain embodiments, the excitation lines are positioned about 2 µm apart from each other. In certain embodiments, the excitation lines are positioned about 5 µm apart from each other. In certain embodiments, the excitation lines are positioned about 10 µm apart from each other. In certain embodiments, the excitation lines are positioned the one or more excitation sources are positioned about 20 µm apart from each other. In certain embodiments, the excitation lines are positioned about 25 µm apart from each other. In certain embodiments, the excitation lines are positioned about 50 µm apart from each other. In certain embodiments, the excitation lines are positioned about 75 µm apart from each other. In certain embodiments, the excitation lines are positioned about 100 µm apart from each other.

In some embodiments, one or more lasers directly produce the excitation lines without using a lens.

In some embodiments, the excitation source utilizes natural illumination. In certain embodiments, natural illumination comprises sunlight; starlight, fire, electricity storms, and bioluminescence.

In some embodiments, the line generator comprises a reflective surface that reflects the excitation lines from the lens onto the sample. In certain embodiments, the line generator comprises one or more reflective surfaces that reflect the excitations lines from the lens onto the sample. In certain embodiments, the reflective surface is capable of reflecting the excitation lines onto the sample. In certain embodiments, the reflective surface reflects the excitation lines onto the sample in horizontal lines, such that the horizontal lines are non-overlapping. In certain embodiments, the reflective surface reflects the excitation lines onto the sample in an array of dots or circles, such that the dots or circles are non-overlapping. In certain embodiments, the reflective surface reflects the excitation lines onto the sample in an array of dots, such that the dots are non-overlapping. In certain embodiments, the reflective surface reflects the excitation lines onto the sample in an array of circles, such that the circles are non-overlapping.

In some embodiments, the reflective surface is a dichroic mirror. In certain embodiments, the dichroic mirror reflects the excitation lines from the lens onto the stage. In certain embodiments, the dichroic mirror positions the excitation lines relative to each other such that each excitation line excites a spatially distinct horizontal line in the image plane of the sample.

In certain embodiments, a quad-band dichroic mirror reflects the excitation lines from the lens onto the sample. In certain embodiments, the quad-band dichroic mirror is a Semrock, Di-405-488-561-635 Dichroic Mirror. In certain embodiments, the dichroic mirror eliminates the need for dichroic switching.

In some embodiments, the excitation sources and emissions pass through one or more common multi-band dichroic mirrors and/or filters.

In any of the previous embodiments, the line generator further comprises a periscope that can focus the light from an excitation source onto a lens. In certain embodiments, a two mirror periscope guides the light from excitation source onto a lens. In certain embodiments, a two mirror periscope guides excitation lines onto a dichroic mirror.

In some embodiments, a sample can be any sample deemed suitable by those of skill in the art. Exemplary samples are described in sections below.

In some embodiments, a target can be any target deemed suitable by those of skill in the art. Exemplary targets are described in sections below.

In some embodiments, a probe can be any probe deemed suitable by those of skill in the art. Exemplary probes are described in sections below.

In some embodiments, a microscope is any microscope deemed suitable by those of skill in the art. Examples of microscopes include but are not limited to inverted, upright, and microscopes from the following manufacturers: Nikon, Olympus, Leica.

In some embodiments, a microscope stage is where an experimenter places a sample for imaging. In certain embodiments, the scanning stage is also known as an XY stage.

In some embodiments, the scanning stage has a sample area of about 10,000 $cm^2$. In some embodiments, the scanning stage has a sample area of about 8,100 $cm^2$. In some embodiments, the scanning stage has a sample area of about 4,900 $cm^2$. In some embodiments, the scanning stage has a sample area of about 3,600 $cm^2$. In some embodiments, the scanning stage has a sample area of about 2,500 $cm^2$. In some embodiments, the scanning stage has a sample area of about 1,600 $cm^2$. In some embodiments, the scanning stage has a sample area of about 900 $cm^2$. In some embodiments, the scanning stage has a sample area of about 400 $cm^2$. In some embodiments, the scanning stage has a sample area of about 100 $cm^2$. In some embodiments, the scanning stage has a sample area of about 81 $cm^2$. In some embodiments, the scanning stage has a sample area of about 64 $cm^2$. In some embodiments, the scanning stage has a sample area of about 49 $cm^2$. In some embodiments, the scanning stage has a sample area of about 36 $cm^2$. In some embodiments, the scanning stage has a sample area of about 25 $cm^2$. In some embodiments, the scanning stage has a sample area of about 16 $cm^2$. In some embodiments, the scanning stage has a sample area of about 9 $cm^2$. In some embodiments, the scanning stage has a sample area of about 4 $cm^2$. In some embodiments, the scanning stage has a sample area of about 1 $cm^2$.

In some embodiments, a control unit controls the velocity of the stage across the field of view of the microscope. In some embodiments, the controller unit controls a motor that moves the stage across the field of view of the microscope. In some embodiments, the controller unit controls one or more motors that move the stage across the field of view of the microscope.

In some embodiments, the controller moves the stage in any direction or any directions across the field of view of the microscope. In some embodiments, the controller moves the stage in a single direction across the field of view of the microscope. In certain embodiments, the controller moves the stage linearly across a field of view of the microscope. In certain embodiments, the controller moves the stage in a circular motion across the field of the microscope. In such embodiments, the detector or detectors are configured to detect emissions along the excitation lines.

In certain embodiments, the controller moves the stage at a constant velocity. In some embodiments, the stage moves at a velocity of about 1 pixel per unit of exposure time. In certain embodiments, the stage moves at a velocity of 1 pixel per unit of exposure time. In certain embodiments, the stage moves at a velocity of slower than 1 pixel per unit of exposure time. In certain embodiments, the stage moves at a velocity of faster than 1 pixel per unit of exposure time. In certain embodiments, the velocity varies by no more than ±5%. In certain embodiments, the velocity varies by no more than ±10%. In certain embodiments, the velocity varies by no more than ±15%. In certain embodiments, the velocity varies by no more than ±20%. In particular embodiments, velocity variation is about the mean, i.e. average, velocity. In certain embodiments, the controller moves the stage at a non-constant velocity.

In some embodiments, the stage comprises a flow cell in which a sample is placed and fluid moves in and out of the cell. In some embodiments, a syringe pump transmits fluids into and out of the flow cell. In certain embodiments, one or more syringe pumps transmit fluids into and out of the flow cell. In some embodiments, the flow cell comprises a fluid switcher allowing different fluids to come into contact with the sample. In certain embodiments, one or more reagents, probes or labelling reagents come into contact with the sample.

The signal detector can be any signal detector deemed suitable by those of skill in the art. In some embodiments, the signal detector is configured to collect one or more images the images from the microscope. In some embodiments, the signal detector is capable of detecting the visual signals emitted from the probes. In certain embodiments, the detector is a single camera instead of multiple line detectors. In certain embodiments, the detector comprises a charge-coupled device (CCD). In certain embodiments, the detector comprises a complementary metal-oxide semiconductor (CMOS) camera. In certain embodiments, the detector comprises other detector modalities that a person of skill would recognize.

In some embodiments, the detector detects the signals from the sample. In some embodiments, the detector detects the images from the sample. In certain embodiments, the detector transmits the signals or images to a display. In certain embodiments, the detector transmits signals or images to a data storage component.

In some embodiments, the microscope in the above embodiments is setup according to FIG. 2A. FIG. 2A illustrates a setup based on a Nikon microscope and an ASI MS2000 stage. A cylindrical lens focuses an excitation source into a line on the sample. The sample is then scanned over the line by moving the stage moving in a linear direction. This setup obtained data from 4 channels a sample area of 2 cm×0.5 cm in under 110 seconds, using 4 channels at the same time via the parallel lasers. In some embodiments, the microscope of any of the above embodiments is further setup according to FIG. 2B.

In some embodiments, the multi-channel line scanner setup also provides line-confocal capabilities in a multi-channel fashion. By selecting only the central pixel line (or a number of pixels) for each excited line, a slit is effectively put in front of the detector. This is equivalent to a conventional line confocal instrument with a 4 µm (pixel size of the camera) physical slit that is positioned in one of the conjugate planes of the image and sample.

In some embodiments, the effective size of the slit is 1 pixel line. In some embodiments, the effective size of the slit chosen is 1 pixel line or multiple pixels, depending on how much background rejection versus signal collected is needed. In certain embodiments, software can update the effective slit size in real time, allowing for considerable flexibility over conventional designs.

In some embodiments, provided herein is an apparatus comprising a sample support, an illumination component, and a detection component.

In certain embodiments, the illumination component comprises one or more excitation sources. In certain embodiments, the one or more excitation sources produce a plurality of lines at different wavelengths. In certain embodiments, the plurality of lines is parallel to each other. In certain embodiments, the plurality of lines at different wavelengths converge at the same position on the sample. In certain embodiments, the detector comprises a charge-coupled device (CCD), a complementary metal-oxide semiconductor (CMOS) camera, or other detector modalities. In certain embodiments, the detector comprises one or more filters, wherein each filter filters out a specific emission from the sample. In certain embodiments, the apparatus incorporates any of the previous embodiments.

In certain embodiments, the illumination geometry of the apparatus comprises but is not limited to epi-illumination from the objective and direct illumination.

In any of the previous embodiments, the apparatus comprises a pinhole that blocks out of focus light. In certain embodiments, the pinhole is used when the excitation line is a dot or circle.

In any of the previous embodiments, the apparatus comprises a slit that blocks out of focus light. In certain embodiments, the slit is used when the excitation line is a geometric line.

In any of the previous embodiments, many advantages are offered over conventional microscopy. One advantage over conventional microscopy is that a common multi-band dichroic mirror and filters removes optical aberrations introduced by different dichroic components and filters in a conventional microscope.

Another advantage over conventional microscopy is that the setup also requires no moving parts in the microscope, removing sources of vibrations which perturbs image quality.

Another advantage over conventional microscopy is that compared to a conventional line scanning instrument, which requires all lasers to focus onto the same line, any of the previous embodiments do not require the lasers lines to be aligned to a high degree of precision as the distance between excitation sources can vary. All of the laser lines are parallel by default if all lasers are passing through a single lens to focus them along one direction.

Another advantage over conventional microscopy is that it does not require multiple dichroic components to separate the emission fluorescence, further reducing the complexity of design and the need for precise alignment of all the detectors, making the instrument robust. Another advantage is that there is no need to synchronize the stage and camera.

Another advantage is that in a conventional line scanning confocal instrument, the laser line is often rostered over the sample by a mirror galvanometer, requiring the confocal slit to move in a synchronized fashion, thus complicating the implementation.

Another advantage is that in any of the previous embodiments, the apparatus can be built without any moving pieces.

Another advantage is that multiple confocal images can be generated in each of the channels at the same time.

Imaging

In some embodiments, the data obtained from the detector is tiled to construct a larger image of the sample. In some embodiments, the data obtained from the detector is combined in order to show the overlap of each channel on a given sample area. In certain embodiments, the multi-channel line scanner uses different velocities when imaging a sample, and image reconstruction accounts for the different stage residence times at each position.

In some embodiments, the region of interest (ROI) on the detector is cropped to contain only the lines from excitation sources within the ROI, thereby increasing speed of acquisition. In certain embodiments, the detector continuously acquires images from the sample by moving the stage continuously across the microscope.

In some embodiments, different imaging technologies, methods, and platforms can be integrated for the imaging steps. In certain embodiments, these imaging technologies, methods, and platforms comprise, but are not limited to epi-fluorescence microscopy, confocal microscopy, the different types of super-resolution microscopy (PALM/STORM, SSIM/GSD/STED), and light sheet microscopy (SPIM and etc.).

In certain embodiments, exemplary super resolution technologies include but are not limited to I5M and 4Pi-microscopy, Stimulated Emission Depletion microscopy (STEDM), Ground State Depletion microscopy (GSDM), Spatially Structured Illumination microscopy (SSIM), Photo-Activated Localization Microscopy (PALM), Reversible Saturable Optically Linear Fluorescent Transition (RESOLFT), Total Internal Reflection Fluorescence Microscope (TIRFM), Fluorescence-PALM (FPALM), Stochastical Optical Reconstruction Microscopy (STORM), Fluorescence Imaging with One-Nanometer Accuracy (FIONA), and combinations thereof. For examples: Chi, 2009 "Super-resolution microscopy: breaking the limits, Nature Methods 6(1):15-18; Blow 2008, "New ways to see a smaller world," Nature 456:825-828; Hell, et al., 2007, "Far-Field Optical Nanoscopy," Science 316: 1153; R. Heintzmann and G. Ficz, 2006, "Breaking the resolution limit in light microscopy," Briefings in Functional Genomics and Proteomics 5(4):289-301; Garini et al., 2005, "From micro to nano: recent advances in high-resolution microscopy," Current Opinion in Biotechnology 16:3-12; and Bewersdorf et al., 2006, "Comparison of I5M and 4Pi-microscopy," 222(2): 105-117; and Wells, 2004, "Man the Nanoscopes," JCB 164(3):337-340.

Software

In some embodiments, software controls the apparatus and/or storage and/or analysis of data. In certain embodiments, codes are written in Micromanager, a free software supported by the National Institute of Health, to control a microscope as well as fluidics elements. In certain embodiments, valves, stages, light sources, cameras and/or microscopes are controlled through Micromanager. Other control software include Metamorph, Nikon Elements, Olympus, Zeiss, Leica software.

In some embodiments, compressed sensing is used for dense images (Zhu et al., Faster STORM using compressed sensing. Nat. Methods. 2012, 9(7):721-3) and deconvolution methods are used to separate out the spots in dense clusters. In some embodiments, improvement in image analysis increases multiplex capacity of provided methods. In some embodiments, efficiency is improved in a similar fashion to improvement from the Illumina GAII sequencer to the HiSeq machines, wherein using image processing methods to analyze densely packed clusters on the sequencing chip increased the throughput. In some embodiments, data acquisition and analysis are integrated in a user-friendly package.

In some embodiments, provided herein are software packages for data analysis. In some embodiments, provided herein are software packages for data analysis in Python and Matlab. Images can be a variety of sizes, and can the optionally optimized if desirable. In some embodiments, each FOV is 6 Megapixels at 14 bits depth, corresponding to 1.5 MB of data per image. In some embodiments, about 100 GB of data are generated per run. In some embodiments, provided technologies provide methods for data processing and/or mitigating data log jam. In some embodiments, data log jam is mitigated by segmenting out the spots from each image, fitting them with 2 dimensional Gaussian distributions and recording the center position of the fits. In some embodiments, provided technologies save computer space by discarding raw images and saving processed data.

Computer Hardware

In some embodiments, the multi-channel line scanner is implemented as a computer system and/or a computer program product that comprises a computer program mechanism embedded in a computer readable storage medium. In some embodiments, any of the previous embodiments, are implemented in one or more computers or computer systems. In some embodiments, any of the previous embodiments, are implemented in one or more computer program products. In some embodiments, provided herein is a computer system or a computer program product that encodes or has instructions for performing any or all of the methods disclosed herein. In certain embodiments, the methods/instructions are stored on a CD-ROM, DVD, magnetic disk storage product, or any other computer readable data or program storage product. In some embodiments, the methods/instructions are embedded in permanent storage, such as ROM, one or more programmable chips, or one or more application specific integrated circuits (ASICs). In certain embodiments, permanent storage is localized in a server, 802.11 access point, 802.11 wireless bridge/station, repeater, router, mobile phone, or other electronic devices. In certain embodiments, the computer program product is distributed electronically, via the Internet or otherwise, by transmission of a computer data signal (in which the software modules are embedded) either digitally or on a carrier wave.

In some embodiments, the multi-channel line scanner of any of the previous embodiments comprises a computer processor configured to control the control unit, the line generator, and the detector.

In some embodiments, the multi-channel line scanner of any of the previous embodiments comprises a data-storage component capable of storing instructions to control the: the control unit, the line generator, and the detector.

In some embodiments, the multi-channel line scanner comprises a data-storage component capable of storing signals and/or images from the detector.

In some embodiments, a computer system or a computer program product that contains any or all of the program modules as disclosed herein. In some embodiments, there is a module to control the microscope. In some embodiments, there is a module to control the excitation sources. In some embodiments, there is a module to control the mirror(s). In some embodiments, there is a module to control the detector. In some embodiments, there is a module to control the stage. In some embodiments, there is a module to control the lens(es). In some embodiments, there is a module to control the pump(s). In some embodiments, there is a module to control the fluid switcher(s). In some embodiments, there is a module to control the data storage. In some embodiments, there is a module to control the signal analysis. In some embodiments, there is a module to control the image analysis. In some embodiments, there is a module to adjust the confocality of the image by selecting the number of lines or pixels kept from the image. In certain embodiments, the module to adjust the confocality of the image selects a slit or pinhole size depeneding on the geometry of the excitaiton line. In certain embodiments, the module to adjust the confocality of the image selects a slit if the geometry of excitation line is a geometric line. In certain embodiments, the module to adjust the confocality of the image selects a pinhole if the geometry of excitation line is a dot or a circle.

These program modules can be stored on a CD-ROM, DVD, magnetic disk storage product, or any other computer readable data or program storage product. The program modules can also be embedded in permanent storage, such as ROM, one or more programmable chips, or one or more application specific integrated circuits (ASICs). Such permanent storage can be localized in a server, 802.11 access point, 802.11 wireless bridge/station, repeater, router, mobile phone, or other electronic devices. The software modules in the computer program product can also be distributed electronically, via the Internet or otherwise, by transmission of a computer data signal (in which the software modules are embedded) either digitally or on a carrier wave.

Methods

Sample

In some embodiments, a method of imaging a sample comprises placing the sample on a microscope stage. In certain embodiments, a method of imaging a sample comprises imaging a sample that comprises one or more targets and one or more probes, wherein the probes are capable of emitting visually detectable signals, and wherein each individual probe is hybridized to a unique target in the sample. In certain embodiments, a method of imaging a sample comprises imaging a sample that comprises one or more targets that are nucleic acids. In certain embodiments, a method of imaging a sample comprises imaging a sample comprising nucleic acids that are mRNAs. In certain embodiments, a method of imaging a sample comprises imaging a sample comprising one or more targets that are proteins or polypeptides.

In some embodiments, a method of imaging a sample comprises moving the microscope stage in a single direction. In certain embodiments, a method of imaging a sample comprises moving the microscope stage at a constant velocity. In certain embodiments, a method of imaging a sample comprises moving the microscope stage at a constant velocity as described above. In any of the previous embodiments, a method of imaging a sample comprises moving the microscope stage at a non-constant velocity.

In some embodiments, a method of imaging a sample comprises exciting one or more probes with excitation lines. In some embodiments, a method of imaging a sample comprises positioning two or more excitation lines relative to each other such that each excitation line excites a spatially distinct horizontal line in the image plane of the sample. In certain embodiments, a method of imaging a sample comprises positioning two or more excitation lines about 0.5 µm to about 100 µm apart from each other. In certain embodiments, a method of imaging a sample comprises positioning two or more excitation lines about 0.5 µm apart from each other. In certain embodiments, a method of imaging a sample comprises positioning two or more excitation lines about 1 µm apart from each other. In certain embodiments, a method of imaging a sample comprises positioning two or more excitation lines about 2 µm apart from each other. In certain embodiments, a method of imaging a sample comprises positioning two or more excitation lines about 5 µm apart from each other.

In some embodiments, a method of imaging a sample comprises detecting one or more signals emitted by the one or more probes. In certain embodiments, a method of imaging a sample comprises detecting one or more signals emitted by the one or more probes by using a detector comprising a charge-coupled device (CCD), complementary metal-oxide semiconductor (CMOS) camera, or other detector modalities.

In some embodiments, a method for multi-channel imaging a sample comprises providing a sample. In certain embodiments, the sample is a silicon wafer. In certain embodiments, the sample is a planet or a portion thereof. In such embodiments, the detector or detectors can be configured in an aerial location or in outer space, in orbit of the planet, for instance in one or more satellites.

In some embodiments, a method for multi-channel imaging a sample comprises illuminating the sample with a plurality of lines of different wavelengths. In certain embodiments, the different wavelengths comprise x-ray, ultra violet, visible range, infrared, far infrared, radio waves, and microwaves. In certain embodiments, the plurality of lines of different wavelengths are parallel to each other. In certain embodiments, the lines comprise geometric shapes. In certain embodiments, the geometric shape is a circle. In certain embodiments, the geometric shape is a line. In certain embodiments, the plurality of lines with different wave lengths converge at the same position on the sample. In certain embodiments, each line is illuminated by a plurality of wave lengths. In certain embodiments, each line is illuminated by a single wave length. In certain embodiments, illuminating the sample utilizes one excitation source. In certain embodiments, illuminating the sample utilizes natural illumination. In certain embodiments, natural illumination comprises sunlight; starlight, fire, electricity storms, and bioluminescence.

In some embodiments, a method for multi-channel imaging a sample comprises detecting emission in a plurality of channels with one or more detectors, the detector is configured to detect emissions along the above lines of any previous embodiment. In certain embodiments, the detector comprises one or more filters, wherein each filter filters out a specific emission from the sample. In certain embodiments, detector comprises a charge-coupled device (CCD), a complementary metal-oxide semiconductor (CMOS) camera, or other detector modalities In some embodiments, a method of imagining a sample comprises focusing the light from an excitation source along one direction to form an excitation line.

In some embodiments, samples comprise targets and probes in solution. Each is described below.

In some embodiments, the multi-channel line scanner analyzes a biological sample of interest.

In some embodiments, the multi-channel line scanner profiles nucleic acids (e.g., transcripts and/or DNA loci) in cells. In some embodiments, the multi-channel line scanner profiles multiple targets in single cells. In some embodiments, the multi-channel line scanner profiles a large number of targets (transcripts, DNA loci or combinations thereof), with a limited number of detectable labels through sequential barcoding.

Probes

In some embodiments, a probe is any probe deemed suitable by those of skill in the arts.

Methods for designing and preparing detectably labelled oligonucleotides labelled are widely known in the art. In some embodiments, the probes are prepared using the methods of Lubeck E. et al., 2012 and hereby incorporated fully. In some embodiments, the probes are prepared using the methods described in US patent application publication US 2012/0142014, and hereby incorporated fully.

In some embodiments, the multi-channel line scanner detects a labelled oligonucleotide that has been labelled prior to, concurrent with or subsequent to its binding to its target. In some embodiments, a detectably labelled oligonucleotide, such as a fluorophore-labelled oligonucleotide, is labelled prior to its binding to its target. In some embodiments, a detectably labelled oligonucleotide is labelled concurrent with its binding to its target. In some embodiments, a detectably labelled oligonucleotide is labelled subsequent to its binding to its target. In some embodiments, a detectably labelled oligonucleotide is labelled subsequent to hybridization through orthogonal amplification with hybridization chain reactions (HCR) (Choi, H M., Nat Biotechnology. 2010 November; 28(11):1208-12). In some embodiments, a detectably labelled oligonucleotide comprises a moiety, e.g., a nucleic acid sequence, that one or more moieties that can provide signals in an imaging step can be directly or indirectly linked to the oligonucleotide.

Fluorophores

In some embodiments, the fluorophore is any fluorophore deemed suitable by those of skill in the arts.

In some embodiments, the fluorophores detected by the multi-channel line scanner include but are not limited to fluorescent dyes, including but not limited to fluorescein, rhodamine, Alexa Fluors, DyLight fluors, ATTO Dyes, or any analogs or derivatives thereof.

In some embodiments, the fluorophores detected by the multi-channel line scanner include but are not limited to fluorescein and chemical derivatives of fluorescein; Eosin; Carboxyfluorescein; Fluorescein isothiocyanate (FITC); Fluorescein amidite (FAM); Erythrosine; Rose Bengal; fluorescein secreted from the bacterium *Pseudomonas aeruginosa*; Methylene blue; Laser dyes; Rhodamine dyes (e.g., Rhodamine, Rhodamine 6G, Rhodamine B, Rhodamine 123, Auramine O, Sulforhodamine 101, Sulforhodamine B, and Texas Red).

In some embodiments, the fluorophores detected by the multi-channel line scanner include but are not limited to ATTO dyes; Acridine dyes (e.g., Acridine orange, Acridine yellow); Alexa Fluor; 7-Amino actinomycin D; 8-Anilinonaphthalene-1-sulfonate; Auramine-rhodamine stain; Benzanthrone; 5,12-Bis(phenylethynyl) naphthacene; 9,10-Bis(phenylethynyl)anthracene; Blacklight paint; Brainbow; Calcein; Carboxyfluorescein; Carboxyfluorescein diacetate succinimidyl ester; Carboxyfluorescein succinimidyl ester; 1-Chloro-9,10-bis(phenylethynyl)anthracene; 2-Chloro-9,10-bis(phenylethynyl)anthracene; 2-Chloro-9,10-diphenylanthracene; Coumarin; Cyanine dyes (e.g., Cyanine such as Cy3 and Cy5, DiOC6, SYBR Green I); DAPI, Dark quencher, DyLight Fluor, Fluo-4, FluoProbes; Fluorone dyes (e.g., Calcein, Carboxyfluorescein, Carboxyfluorescein diacetate succinimidyl ester, Carboxyfluorescein succinimidyl ester, Eosin, Eosin B, Eosin Y, Erythrosine, Fluorescein, Fluorescein isothiocyanate, Fluorescein amidite, Indian yellow, Merbromin); Fluoro-Jade stain; Fura-2; Fura-2-acetoxymethyl ester; Green fluorescent protein, Hoechst stain, Indian yellow, Indo-1, Lucifer yellow, Luciferin, Merocyanine, Optical brightener, Oxazin dyes (e.g., Cresyl violet, Nile blue, Nile red); Perylene; Phenanthridine dyes (Ethidium bromide and Propidium iodide); Phloxine, Phycobilin, Phycoerythrin, Phycoerythrobilin, Pyranine, Rhodamine, Rhodamine 123, Rhodamine 6G, RiboGreen, RoGFP, Rubrene, SYBR Green I, (E)-Stilbene, (Z)-Stilbene, Sulforhodamine 101, Sulforhodamine B, Synapto-pHluorin, Tetraphenyl butadiene, Tetrasodium tris(bathophenanthroline disulfonate) ruthenium(II), Texas Red, TSQ, Umbelliferone, or Yellow fluorescent protein.

In some embodiments, the fluorophores detected by the multi-channel line scanner include but are not limited to Alexa Fluor family of fluorescent dyes (Molecular Probes, Oregon). Alexa Fluor dyes are widely used as cell and tissue labels in fluorescence microscopy and cell biology. The excitation and emission spectra of the Alexa Fluor series cover the visible spectrum and extend into the infrared. The individual members of the family are numbered according roughly to their excitation maxima (in nm). Certain Alexa Fluor dyes are synthesized through sulfonation of coumarin, rhodamine, xanthene (such as fluorescein), and cyanine dyes. In some embodiments, sulfonation makes Alexa Fluor dyes negatively charged and hydrophilic. In some embodiments, Alexa Fluor dyes are more stable, brighter, and less pH-sensitive than common dyes (e.g. fluorescein, rhodamine) of comparable excitation and emission, and to some extent the newer cyanine series. Exemplary Alexa Fluor dyes include but are not limited to Alexa-350, Alexa-405, Alexa-430, Alexa-488, Alexa-500, Alexa-514, Alexa-532, Alexa-546, Alexa-555, Alexa-568, Alexa-594, Alexa-610, Alexa-633, Alexa-647, Alexa-660, Alexa-680, Alexa-700, or Alexa-750.

In some embodiments, the fluorophores detected by the multi-channel line scanner comprise one or more of the DyLight Fluor family of fluorescent dyes (Dyomics and Thermo Fisher Scientific). Exemplary DyLight Fluor family dyes include but are not limited to DyLight-350, DyLight-405, DyLight-488, DyLight-549, DyLight-594, DyLight-633, DyLight-649, DyLight-680, DyLight-750, or DyLight-800.

In some embodiments, the fluorophores detected by the multi-channel line scanner comprises a nanomaterial. In some embodiments, the fluorophore is a nanoparticle. In some embodiments, the fluorophore is or comprises a quantum dot. In some embodiments, the fluorophore is a quantum dot. In some embodiments, the fluorophore comprises a quantum dot. In some embodiments, the fluorophore is or comprises a gold nanoparticle. In some embodiments, the fluorophore is a gold nanoparticle. In some embodiments, a detectable moiety comprises a gold nanoparticle.

In any of the previous embodiments, selection of label for a particular probe in a particular cycle may be determined based on a variety of factors, including, for example, size, types of signals generated, manners attached to or incorporated into a probe, properties of the cellular constituents including their locations within the cell, properties of the cells, types of interactions being analyzed, and etc. In some embodiments, probes are labelled with either Cy3 or Cy5 that has been synthesized to carry an N-hydroxysuccinimidyl ester (NHS-ester) reactive group. Since NETS-esters react readily with aliphatic amine groups, nucleotides can be modified with aminoalkyl groups. This can be done through incorporating aminoalkyl-modified nucleotides during synthesis reactions.

Targets

In some embodiments, a target is any target deemed suitable by those of skill in the arts.

In some embodiments, the multi-channel line scanner detects a labelled oligonucleotide that can hybridize with a target. In some embodiments, a target comprises a transcript. In some embodiments, a target comprises a DNA locus. In some embodiments, a transcript comprises an RNA. In some embodiments, a transcript comprises an mRNA. In some embodiments, a transcript comprises tRNA. In some embodiments, a transcript comprises rRNA. In some embodiments, a transcript comprises snRNA. In some embodiments, an RNA comprises a non-coding RNA. Exemplary non-coding RNA types are widely known in the art, including but not limited to long non-coding RNA (lncRNA), microRNA (miRNA), short interfering RNA (siRNA), piwi-interacting RNA (piRNA), small nucleolar RNA (snoRNA) and other short RNAs. In some embodiments, an RNA comprises lncRNA. In some embodiments, an RNA comprises miRNA. In some embodiments, an RNA comprises piRNA. In some embodiments, an RNA comprises snoRNA.

In some embodiments, the multi-channel line scanner detects a target that comprises a DNA locus. In some embodiments, when a target is a DNA locus, a detectably labelled oligonucleotide optionally comprises one or more RNA nucleotide or RNA segments. A detectably labelled oligonucleotide comprises RNA sequences can be selectively removed, for example, through RNA-specific enzymatic digestion, after imaging without degrading the DNA target. Exemplary enzymes that specifically degrade RNA but not DNA include but are not limited to various RNase, such as RNase A and RNase H.

In some embodiments, the multi-channel line scanner profiles different transcripts formed as a result of splicing variation, RNA editing, oligonucleotide modification, or a combination thereof. In some embodiments, a target is an RNA splicing variant. In some embodiments, provided technologies profile one or more splicing variants of a gene, e.g., locations and quantities of one or more splicing variant of a gene. In some embodiments, provided methods or compositions profile different splicing variants. In some embodiments, a splicing variant contains one or more distinguishable sequences resulted from splicing, and such sequences are targeted. In some embodiments, by targeting exons and/or distinguishable sequences, provided technologies can profile one or more specific splicing variants, or an entire splicing repertoire of an mRNA. As widely known in the art, mRNA splicing are important to numerous biological processes and diseases, for example, neurological diseases like autism or Down syndrome. Molecules responsible for cell-to-cell adhesion and synpatogenesis are spliced and their defects are known to generate miswiring in the brain and cause diseases.

In some embodiments, the multi-channel line scanner detects the labelled oligonucleotides target sequence modifications caused by sequence editing, chemical modifications and/or combinations thereof. In some embodiments, a modified nucleic acid target, optionally after a conversion process, hybridizes with one or more different complementary sequences compared to an un-modified target, and is profiled using one or more oligonucleotides that selectively hybridizes with the modified nucleic acid. In some embodiments, a target is an RNA through by RNA editing (Brennicke, A., A. Marchfelder, et al. (1999). "RNA editing". FEMS Microbiol Rev 23 (3): 297-316). In some embodiments, provided technologies profiles different RNA variants formed by RNA editing. In some embodiments, provided technologies profile modified oligonucleotide. In some embodiments, provided technologies profiles methylated RNA (Song C X, Yi C, He C. Mapping recently identified nucleotide variants in the genome and transcriptome. Nat Biotechnol. 2012 November; 30(11):1107-16). In some embodiments, provided technologies profile methylated DNA. In some embodiments, a target is single-nucleotide polymorphism (SNP).

In some embodiments, the multi-channel line scanner profiles a target and includes quantitative and/or positioning information of a target, in some cases, in single cells, a tissue, an organ, or an organism. In some embodiments, profiling of transcripts can be used to qualitatively and/or quantitatively define the spatial-temporal patterns of gene expression within cells, tissues, organs or organisms.

In some embodiments, each detectably labelled oligonucleotide in a set has a different target, e.g., a transcript or DNA locus. In some embodiments, two or more detectably labelled oligonucleotides in a set have the same target. In some embodiments, two or more detectably labelled oligonucleotides target the same transcript. In some embodiments, two or more detectably labelled oligonucleotides target the same DNA locus. In some embodiments, about 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90 or 100 detectably labelled oligonucleotides the same target.

In some embodiments, the multi-channel line scanner detects multiple fluorescently labelled oligonucleotides for the same target thereby increasing signal intensity. In some embodiments, each fluorescently labelled oligonucleotide in a set targeting the same target interacts with a different portion of a target.

In some embodiments, all detectably labelled oligonucleotides for a target in a set have the same detectable moieties. In some embodiments, all detectably labelled oligonucleotides are labelled in the same way. In some embodiments, all the detectably labelled oligonucleotides for a target have the same fluorophore.

In some embodiments, detectably labelled oligonucleotides for a target are positioned within a targeted region of a target. A targeted region can have various lengths. In some embodiments, a targeted region is about 20 to 1000 base pairs in length. In some embodiments, detectably labelled oligonucleotides for a target are positioned in proximity to each other on the target.

Hybridization

In some embodiments, the probes are hybridized in conditions according to techniques deemed suitable by those of skill in the art.

In some embodiments, the multi-channel line scanner detects a labelled oligonucleotide directly hybridizes to its target. In some embodiments, a detectably labelled oligonucleotide specifically interacts with (recognizes) its target through binding or hybridization to one or more intermediate, e.g., an oligonucleotide, that is bound, hybridized, or otherwise specifically linked to the target. In some embodiments, an intermediate oligonucleotide is hybridized against its target with an overhang such that a second oligonucleotide with complementary sequence ("bridge oligonucleotide" or "bridge probe") can bind to it. In some embodiments, an intermediate targets a nucleic acid and is optionally labelled with a detectable moiety, and comprises an overhang sequence after hybridization with the target. In some embodiments, an intermediate comprises a sequence that hybridizes to a target, an overhang sequence, and optionally a detectable moiety. In some embodiments, an intermediate comprises a sequence that hybridizes to a target and an overhang sequence. In some embodiments, an intermediate does not have a detectable moiety. In some embodiments, a second oligonucleotide is a detectably labelled oligonucleotide. In some embodiments, a second detectably labelled oligonucleotide is labelled with a dye. In some embodiments, a detectably labelled oligonucleotide is labelled with an HCR polymer. In some embodiments, intermediate oligonucleotides bound to targets are preserved through multiple contacting, removing and/or imaging steps; sequential barcodes are provided through combinations of detectable labels that are linked to intermediate oligonucleotides through bridge probes in the contacting and imaging steps. For example, when detectably labelled oligonucleotides are used as bridge probes, barcodes are provided by detectably labelled oligonucleotides that hybridize with intermediate oligonucleotides through their overhang sequences. After an imaging step, bridge oligonucleotides are optionally removed as described herein. In some embodiments, between one and 100 intermediate oligonucleotides are employed for a target.

Antibody-Probes

In some embodiments, a probe binds to an antibody in conditions according to techniques deemed suitable by those of skill in the art. The antibody can be any antibody recognized by those of skill in the art. In certain embodiments, the antibody is full length. In certain embodiments, the antibody is an antigen binding fragment, for instance an scFv fragment.

In some embodiments, the probe binds to the antibody forming a probe-antibody complex. In some embodiments, the probe is covalently linked to the antibody, directly or via a linker. In certain embodiments, the antibody in the probe-antibody complex binds one or more targets.

In some embodiments, the antibody binds one or more targets forming an antibody-target complex. In certain embodiments, the antibody in the antibody target complex then binds a probe. In certain embodiments, the antibody is covalently linked to the probe directly or via a linker.

In any of the previous embodiments, a protein or peptide replaces the antibody in the probe-antibody complex or antibody-target complex. The protein or peptide can be bound to the probe, or covalently linked to the probe directly or via a linker.

In some embodiments, the multi-channel line scanner detects oligonucleotides labelled with fluorophores for fluorescence in situ hybridization (FISH) experiments. FISH detects and localizes the presence or absence of specific DNA sequences or RNA targets.

In some embodiments, the multi-channel line scanner detects oligonucleotides labelled with fluorophores in sequential FISH (seqFISH) experiments. As described in US patent application publication US 2015/0267251 and incorporated herein fully, SeqFISH, through sequential barcoding to multiplex different targets, is able to profile a large number of targets, up to $F^N$, wherein F is the number of types of detectable moieties (in the case of FISH, fluorophores) and N is the number of contacting steps (in the case of FISH, hybridization). For example, when F is four and N is 8, almost the entire transcriptome ($4^8$=65,536) can be profiled. In some embodiments, a plurality of detectably labelled oligonucleotides target between 2 and 100 targets.

In some embodiments, the same type of labels can be attached to different probes for different targets. In some embodiments, probes for the same target have the same label in a plurality of detectably labelled oligonucleotides used in a contacting step (a set of detectably labelled oligonucleotides). Each target, after rounds of contacting and imaging, has its own unique combination of labels (sequential barcoding), so that information, e.g., quantitative and/or spatial information, can be obtained for a target. For example, when fluorophores are used to label detectably labelled oligonucleotides, after N steps, a target would have a sequential barcode of $F_1F_2 \ldots F_N$, wherein $F_n$ is the color of fluorophore used for the target in the $n^{th}$ imaging. One target can be differentiated from another by a difference in their barcodes (e.g., RedRedBlueRed compared to RedRedRedBlue).

In some embodiments, the individual probes are capable of emitting at least F types of detectable visual signals, where $F \geq 2$ and $F^n$ is greater than the number of targets in the sample. In some embodiments, the F types of detectable visual signals comprises one selected from the group consisting of a fluorescence signal, a color signal, a red signal, a green signal, a yellow signal, a combined color signal representing two or more colors, and combinations thereof.

In some embodiments, the multi-channel line scanner is used in seqFISH+(Eng et al, Nature 2019) experiments. SeqFISH+ is a method based on sequential Fluorescence in situ hybridization (Lubeck et al. 2014). In some embodiments, using a multi-channel line scanner enables fast imaging. Since imaging time is the major limiting factor in seqFISH+ experiments, the time to analyze an experiment is drastically reduced, improving the imaging time of cells being profiled. The multi-channel line scanner allows acquiring images from multiple channels simultaneously on a rapidly scanning the sample.

SeqFISH+ works robustly in tissues and cells. This method achieves the multiplexing of 10,000 genes at the mRNA level in single cells in brain slices. SeqFISH+ transcriptome profiles have allowed the identification of novel cells types in situ and reveal spatial organizations in several brain regions, including the cortex, subventricular zone (SVZ), and the olfactory bulb. SeqFISH+ enables the generation of spatial cell atlases with transcriptome-level coverage and discovery-driven studies of biological processes in situ.

A 10,000 gene probe set was used to image cells in the mouse brain cortex, and the olfactory bulb (OB) in two separate brain sections. The brain sections were prepared similar to the cultured cells with initial primary probe hybridization and clearing, followed by automated imaging and sequential hybridizations of the readout probes. Over 10,000-gene-profiles for 2963 cells, covering an area of approximately 0.5 mm$^2$ were collected.

In some embodiments, SeqFISH+ is analyzed using the multi-channel line scanner to help reject background noise from tissues. In another embodiment, SeqFISH+ is implemented on an instrument such as the multi-channel line scanner of any of the previous embodiments to help reject background noise form an out-of-focus background.

In some embodiments, the multi-channel line scanner is used in experiments that integrate mRNA seqFISH with intron seqFISH and antibody staining. Many types of molecules, such as mRNAs, introns, DNA and proteins, can be directly profiled in cells, in tissues as well as in vitro in extracted samples with seqFISH. The intron seqFISH assay can be performed in the same cells as mRNA seqFISH+ for >10,000 genes, as well as several rounds of antibody staining (Shah et al, Cell 2018). The mRNAs can allow accurate definition of cell types, which would be enhanced by the intron seqFISH measurements. 10,421 genes can be imaged directly with intron seqFISH at their nascent transcription active sites in single mouse embryonic stem cells (S. Shah et al. 2018). Because the lifetime of the introns is short, measured in minutes compared to 3-4 hours of mRNAs (Sharova et al., 2009), the intron profiles provides a snapshot of how the transcriptome is activated.

In some embodiments, the multi-channel line scanner simultaneously detects the level of mRNA, instantaneous transcription activity by introns, and spatial location of active loci by introns or DNA FISH, and multiplexed protein in a single cell allow the ability to characterize cellular states in biological processes. In certain embodiments, nucleic acids species such as DNA and RNA can be multiplexed by seqFISH through barcoding or nonbarcoding schemes. In certain embodiments, proteins can be detected by antibodies, nanobodies or other affinity reagents that are directly labelled or indirectly labelled with oligonucleotides.

In some embodiments, the multi-channel line scanner analyzes each round of hybridization. This allows transcriptomes and proteomes to be covered.

In some embodiments, a multi-channel line scanner detects high abundant species by diluting an affinity reagent. In certain embodiments, lower concentrations of oligonucleotide probes, antibodies, or unlabelled that bind to the targets, but would not yield a fluorescent signal.

In some embodiments, the multi-channel line scanner analyzes amplification methods such as hybridization chain reaction (HCR) (Shah et al, 2016). In some embodiments, the multi-channel line scanner is applied to amplification methods such as and click-amplifying FISH (CLAMP-FISH) (Rouhanifard et al. 2018).

In some embodiments, the multi-channel line scanner analyzes an smFISH-based method called RNA SPOTs (Sequential Probing Of Targets). RNA SPOTs profiles a transcriptome with single molecule sensitivity (Eng et al, Nature Methods 2017).

In some embodiments, the method of imaging in any of the previous embodiments applies to a wide range of imaging applications. In certain embodiments, the method of imaging of any of the previous embodiments applies to microscopic. In certain embodiments, the method of imaging of any of the previous embodiments applies to a macroscopic. In certain embodiments, the method of imaging of any of the previous embodiments applies to the field of cosmology.

In certain embodiments, the methods of imaging in any of the previous examples produce high dimensional data. In certain embodiments, algorithms process high dimensional data thereby classifying and clustering the data. In certain embodiments, the high dimensional data trains machine learning algorithms to recognize distinct classes of objects. For example, during the inspection of a material, a defect might not be apparent if a single color image is used, but may become clear when acquiring multiple images of a different spectrum.

In some embodiments, the method of imaging of any of the previous embodiments applies to a metrological examination of silicon wafers. A metrological examination requires scanning a large area to examine structural features on the wafer. Instead of illuminating a sample with a single laser beam or multiple beams focused on the same spot, the multi-channel line scanner generates a set of multi-channel images from a single scan of the wafer.

In some embodiments, the methods of imaging are provide satellite imaging. In certain embodiments, the methods of imaging provide high-altitude imaging of the surface features of a planet. In certain embodiments, the satellite imaging does not require illumination of the surface features of the planet. In certain embodiments, satellite imaging utilizes different masked lines with different emission filters on the satellite's detector.

In any of the previous embodiments, the methods of imaging are not restricted to fluorescence imaging. In some embodiments, other modalities including but not limited to absorption measurement, Raman scattering, IR scattering and other methods are implemented with the separation of emission lines on a camera instead of distinct line detectors for each wave length.

The following non-limiting methods are provided to further illustrate the embodiments of the invention disclosed herein. It should be appreciated by those of skill in the art that the techniques disclosed in the examples that follow represent approaches that have been found to function well in the practice of several embodiments of the invention, and thus be considered to constitute examples of modes for its practice. However, those of skill in the art should, in light of the present disclosure, appreciate that many changes can be made in the specific embodiments that are disclosed and still obtain a like or similar result without departing from the spirit and the scope of the invention.

Example 1

This example illustrates an exemplary speed at which the multi-channel line scanner collects data.

FIG. 2A and FIG. 2B illustrate setups using optical parts that do not require moving optical components, such as a filter turret. In this prototype, the emissions from four excitation lines collected on a single camera instead of multiple line detectors. This was accomplished by offsetting each of the excitation lines with 1 μm spacing using simple two-mirror periscopes.

The emissions from the probes were collected on a single CMOS camera. This setup used a Region of Interest (ROI) imaging mode of the camera to image only these four excitation lines.

This setup allowed collection of the images quickly and captured each ROI in under 1 ms.

Example 2

This example illustrates the imaging of sections of tissue using the multi-channel line scanner. In this example, a section of brain tissue is imaged (FIG. 3)

Brain sections were prepared according to techniques that would be deemed well known by those of skill in the art. Briefly, brain sections were perfused and fixed in paraformaldehyde, embedded in sucrose, and optical cutting temperature compound. Brain tissue was then cryo-sectioned into 5-10 μm slices and attached to coverslips.

Four fluorophores were used to stain the brain tissue. DAPI (staining the nucleus and detectable in the 405 nm channel), and three other fluorophores bound to oligonucleotides were used. The oligonucleotide probes had fluorophores that are detectable in the 488, 556 and 640 nm channels. The multi-channel line scanner used four laser excitation sources, to produce excitation lines at wavelengths designed to excite the fluorophores.

FIG. 3 illustrates that single molecules (dots) fluoresce as they pass through the excitation lines as the flow cell on the stage, containing the sample, is scanned. FIG. 3 further illustrates that each mRNA molecule bound to a hybridized oligonucleotide probe appears as a diffraction limited "dot" in the corresponding lines. For example, the 556 lines contain "dots" that correspond to mRNA transcripts hybridized to oligonucleotide probes containing Alexa546 fluorophores.

FIG. 4 illustrates the individual images can be tiled together and reconstructed to show a larger image across a sample.

In this example, the stage was moved at a velocity of 1 mm/s and had a 1 ms exposure time. In contrast, conventional imaging typically requires exposure times of 50 ms-10 sec, and stage movement of 0.2 mm per second.

Exemplary Use 2

RNA Profiling and Protein Profiling In Vitro

As illustrated in FIG. 5, mRNA was extracted from murine cells and captured on a Locked Nucleic Acid (LNA) poly(dT) functionalized coverslip (FIG. 5a). The transcripts were hybridized with a pool of 323,156 primary probes targeting the coding regions of 10,212 mRNAs with 28 to 32 probes per gene (FIG. 5a,b). These 323,156 primary probes were computationally designed to avoid cross-talk and mis-hybridization, such that each probe binds specifically only to a single mRNA sequence. This specificity was validated experimentally, with few false positives observed in the RNA SPOTs experiment (Eng et al, 2018).

To distinguish 10,212 genes with RNA SPOTs, 20 rounds of sequential hybridization were used to uniquely barcode every gene with a "temporal barcode," which appears as a diffraction limited "dot" on the glass coverslip that changes color over the multiple rounds of hybridization. During each round of hybridization, each sample was imaged with 3 channels. Every 4 rounds of hybridization are grouped into 4×3=12 pseudo-color image such that every mRNA appears in one and only one of the 12 pseudocolors. This initial pseudocolor labelling of the mRNAs is then removed, and another group of pseudocolor is hybridized via readout probes on the mRNAs. In this fashion, 4 rounds of barcoding are sufficient to cover the transcriptome ($12^4$=20,736), with an additional round of error correction to compensate for a drop in any single round of barcoding (FIG. 4c-d).

The multi-channel line scanner implemented in this disclosure allows for a dramatic increase in the throughput in the number of SPOTs detected per experiment. A million spots were detected in a 14 hour experiment using a conventional fluorescence microscope to capture images in each 200 um×200 um field of view (FOV) and then scanned the stage to capture over 100 FOV in one experiment. At each FOV, fluorescence filters were toggled to image each of the four fluorescence channels, taking approximately 20 seconds per position.

Since in each round of hybridization over 100 FOV are acquired (~2000 seconds of imaging), over the entire experiment approximately 11 hours of imaging time were used.

The new multi-channel line scanner shows a 5-25 fold increase in the number of spots captured. This translates to analyzing 25 million spots per experiment at a significantly shorter total experimental time.

Similar to the in situ applications, protein targets captured in vitro from extracts of cells can also be massively multiplexed and imaged on the line scanner.

REFERENCES

Additional background information can be found in the following references, each of which is hereby incorporated by reference in its entirety.

Eng, Cl et al. Transcriptome-scale super-resolved imaging in tissues by RNA seqFISH. Nature 2019. April; 568(7751): 235-239.

Lubeck, E et al. Single-cell in situ RNA profiling by sequential hybridization. Nature Methods 2014. April; 11(4): 360-1.

Shah, S et al. Dynamics and Spatial Genomics of the Nascent Transcriptome by Intron seqFISH. Cell 2018 Jul. 12; 174(2):363-376.

Sharova, et al. Database for mRNA half-life of 19 977 genes obtained by DNA microarray analysis of pluripotent and differentiating mouse embryonic stem cells. DNA Res 2009. 16: 45-58.

Rouhanifard, S H et al. ClampFISH detects individual nucleic acid molecules using click chemistry-based amplification. Nat Biotechnol. 2018. Nov. 12, 2018.

Eng, Cl et al. Profiling the transcriptome with RNA SPOTs. Nature Methods 2017. 14, pages 1153-1155.

Lubeck, E. et al. Single-cell systems biology by super-resolution imaging and combinatorial labeling. Nat. Methods 9,743-48 (2012).

The invention claimed is:

1. A method of fluorescence imaging of single molecules in a sample, comprising:
    placing the sample on a microscope stage, wherein the sample comprises one or more targets and one or more probes, wherein the probes are capable of emitting visually detectable signals, and wherein each individual probe is hybridized to a unique target in the sample;
    moving the microscope stage in a single direction linearly or circularly;
    exciting one or more probes with excitation lines, wherein two or more excitation lines are positioned relative to each other such that each excitation line excites a spatially distinct horizontal line in an image plane of the sample, and wherein two or more excitation lines are positioned about 0.5 μm to about 100 μm apart from each other; and
    detecting one or more signals emitted by the one or more probes.

2. The method of claim 1, wherein moving the microscope stage is at a constant velocity.

3. The method of claim 2, wherein constant velocity is about 1 pixel per unit of exposure time.

4. The method of claim 1, wherein the one or more targets are nucleic acids.

5. The method of claim 1, wherein the one or more targets are proteins or polypeptides.

6. The method of claim 1, that comprises n rounds of hybridization.

7. The method of claim 6, wherein the individual probes are capable of emitting at least F types of detectable visual signals, where F≥2 and $F^n$ is greater than the number of targets in the sample.

8. The method of claim 1, wherein a lens focuses light from an excitation source along one direction to form an excitation line, or any geometric shape, or uses a line shaped laser.

9. The method of claim 1, wherein the one or more signals emitted by the one or more probes are detected by a detector comprising a charge-coupled device (CCD), complementary metal-oxide semiconductor (CMOS) camera or other detector modalities.

10. The method of claim 1, further comprising analyzing the sample with light sheet microscopy.

11. The method of claim 1, wherein an air objective is used in detecting one or more signals emitted by the one or more probes.

12. The method of claim 1, wherein the probes are used in single molecule fluorescence in situ hybridization (FISH) experiments.

\* \* \* \* \*